(12) United States Patent
Zhang

(10) Patent No.: US 8,024,970 B2
(45) Date of Patent: Sep. 27, 2011

(54) PASSIVE HUMIDITY SENSORS AND METHODS FOR TEMPERATURE ADJUSTED HUMIDITY SENSING

(75) Inventor: Wenwei Zhang, Scotland (GB)

(73) Assignee: Honeywell International Inc., Morristown, NJ (US)

( * ) Notice: Subject to any disclaimer, the term of this patent is extended or adjusted under 35 U.S.C. 154(b) by 774 days.

(21) Appl. No.: 12/138,048

(22) Filed: Jun. 12, 2008

(65) Prior Publication Data

US 2009/0308155 A1   Dec. 17, 2009

(51) Int. Cl.
  *G01R 27/26*   (2006.01)
(52) U.S. Cl. .................................. 73/335.04; 324/664
(58) Field of Classification Search .... 73/29.01–335.05; 324/664, 689, 694
See application file for complete search history.

(56) References Cited

U.S. PATENT DOCUMENTS

| | | | |
|---|---|---|---|
| 5,818,340 A * | 10/1998 | Yankielun et al. | 324/696 |
| 6,631,638 B2 | 10/2003 | James et al. | |
| 6,809,528 B1 * | 10/2004 | Stormbom et al. | 324/664 |
| 7,368,312 B1 * | 5/2008 | Kranz et al. | 257/414 |
| 7,481,107 B2 * | 1/2009 | Itakura et al. | 73/335.04 |
| 7,902,661 B2 * | 3/2011 | Smeys et al. | 257/415 |
| 2004/0089058 A1 * | 5/2004 | De Haan et al. | 324/664 |
| 2009/0141767 A1 * | 6/2009 | Cummins | 73/335.04 |

OTHER PUBLICATIONS

T.J. Harpster, B. Stark, and K. Najafi, "A passive wireless integrated humidity sensor." Sensors and Actuators A 95 (2002) 100-107.*
D. Marioli, E. Sardini, M. Serpelloni, and A. Taroni, "A new measurement method for capacitance transducers in a distance compensated telemetric sensor system." Meas. Sci. Technol. 16 (2005) 1593-1599.*
Todd H. Hubing et al., "Identifying and Quantifying Printed Circuit Board Inductance," pp. 205-208, IEEE, 1994.
Keat Ghee Ong et al., "A Resonant Printed-Circuit Sensor for Remote Query Monitoring of Environmental Parameters," Smart Mater. Struct., pp. 421-428, 2000.

* cited by examiner

*Primary Examiner* — Lisa Caputo
*Assistant Examiner* — Punam Roy
(74) *Attorney, Agent, or Firm* — Shumaker & Sieffert, P.A.

(57) ABSTRACT

A humidity sensor having temperature sensing includes a substrate and a RLC (damped resonant) circuit formed in or on the substrate. The RLC circuit comprises a capacitor having a first and a second electrically conductive plate and a moisture sensitive dielectric interposed between the first and second plate. An RL network comprising an inductor and a resistor is coupled to the capacitor and comprises a high relative temperature coefficient of resistance (TCR) portion formed from a first material which is coupled to a low relative TCR portion formed from a second material different from the first material. The RLC circuit can be a series RLC circuit. In another embodiment, the RLC circuit can comprises a parallel RLC circuit.

20 Claims, 4 Drawing Sheets

PASSIVE HUMIDITY SENSORS AND METHODS FOR TEMPERATURE ADJUSTED HUMIDITY SENSING

FIELD

Embodiments of the present invention relate to non-powered (passive) humidity sensors.

BACKGROUND

Humidity sensors are widely used for humidity and air quality measurement in a wide variety of markets. Such markets include automotive and truck for comfort, safety and powertrain, home appliance for moisture and temperature control, energy efficiency, humidity switches, HVAC, reprography for inkjet and laser/copy, for weather stations, humidity displays and air quality measurement. There are presently trends that the humidity sensor be used without a power source (e.g. battery-less) and have wireless features, such as when the space available does not accommodate a generally bulky battery, or the environment does not facilitate changing the battery.

SUMMARY

This Summary is provided to comply with 37 C.F.R. §1.73, requiring a summary of the invention briefly indicating the nature and substance of the invention. It is submitted with the understanding that it will not be used to interpret or limit the scope or meaning of the claims.

A humidity sensor having temperature sensing includes a substrate and an RLC (damped resonant) circuit formed in or on the substrate. The RLC circuit comprises a capacitor having a first and a second electrically conductive plate and a moisture sensitive dielectric interposed between the first and second plate. An RL network comprising an inductor and a resistor is coupled to the capacitor and comprises a high relative temperature coefficient of resistance (TCR) portion formed from a first material which is coupled to a low relative TCR portion formed from a second material different from the first material.

The RLC circuit can be a series RLC circuit. In another embodiment, the RLC circuit can comprises a parallel RLC circuit.

The high relative TCR portion can be integrated with the inductor (L) or separate from the L. In the embodiment where the high relative TCR portion is at least in part separate from L, the high relative TCR portion generally includes a geometry exclusive of any closed current paths.

As known in the art of electromagnetics, inductance is defined as a ratio of the total magnetic flux that couples (passes through) a closed path to the amplitude of the current that is the source of the magnetic flux. If a wire is configured in a closed loop, the inductance will be a function of the loop geometry as well as the shape and dimensions of the wire itself. Non-inductive resistors according to embodiments of the invention are exclusive of any closed current paths.

A method of temperature compensated humidity sensing comprises exposing a resonant RLC circuit comprising an inductor, a capacitor, and a resistor to environmental conditions including a temperature and a relative humidity. The capacitor comprises a first and second plate and a moisture sensitive dielectric interposed between the plates. A resonant frequency value of the resonant circuit is measured following the exposing. A relative humidity value is determined from the resonant frequency value. A quality factor (Q) value of the resonant circuit is also measured following the exposing. The temperature is determined from the measured Q value, and the measured relative humidity value is adjusted/corrected based on the temperature value.

BRIEF DESCRIPTION OF THE DRAWINGS

FIG. 2A shows a multi-layer high Q series RLC humidity sensor, according to an embodiment of the invention, while

DETAILED DESCRIPTION

Figure 1A:
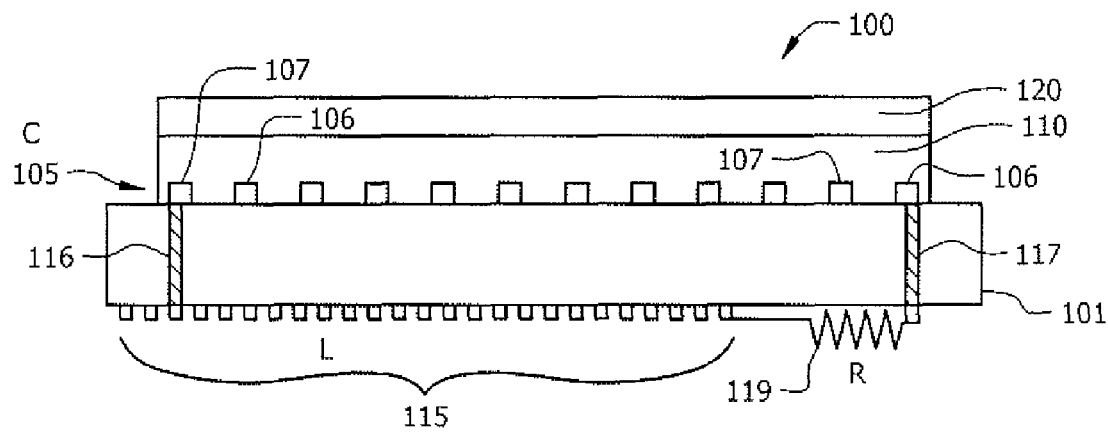
FIG. 1A is a cross sectional view of an RLC-based humidity sensor having temperature sensing according to an embodiment of the invention.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

The invention will now be described more fully hereinafter with reference to accompanying drawings, in which illustrative embodiments of the invention are shown. This invention, may however, be embodied in many different forms and should not be construed as limited to the embodiments set forth herein.

Humidity sensors having temperature sensing according to embodiments of the invention comprise an RLC sensing circuit (also known as a damped resonant circuit) comprising a resistor (R), an inductor (L), and a capacitor (C). The RLC circuit can be connected in either series or in parallel (shunt). The resonant circuit comprises a capacitor having electrically conductive first and a second plates and a moisture sensitive dielectric interposed between the first and second plates.

An RL network comprising an inductor and a resistor is coupled to the capacitor and comprises a high relative temperature coefficient of resistance (TCR) portion formed from a first material which is coupled to a low relative TCR portion formed from a second material different from the first material. In one particular embodiment the high TCR portion can comprise platinum (Pt) or nickel (Ni). The TCR of a typical Pt resistive temperature detector (RTD) is 0.00385 Ohms/Ohms/° C. and is the slope of its R-T curve. The low relative TCR portion of the RL network providing the inductor can be formed from a variety of metals or metal alloys, such as copper or aluminum. Metals such as copper and aluminum have a TCR that is about 4 to 5 times lower as compared to the TCR of platinum.

The RLC circuit forms a damped resonant (oscillator) circuit that has a resonant frequency ($f_0$) that varies with the humidity level. Since relative humidity values are sensitive to the temperature, embodiments of the invention provide temperature data and can use the temperature data to adjust (correct) the relative humidity value for the temperature. Moreover, the temperature around the sensor may also be reported.

In the case of a series RLC circuit, the equations for resonant frequency and Q value are as follows:

$$f_0 = \frac{1}{2\pi\sqrt{LC}} \quad (1)$$

$$Q = \frac{1}{R}\sqrt{\frac{L}{C}} \quad (2)$$

$$Q = \frac{f_0}{\Delta f} \quad (3)$$

Equation (1) above shows the relationship between resonance frequency $f_0$ and the parameters for a series RLC sensing circuit. Resonance occurs when the complex impedance of the LC resonator becomes zero. The resonance frequency $f_0$ can be seen to be independent of the R value, and only a function of the L and C values. Since the L value is essentially fixed, a change in the C value which is generally proportional to the humidity value the sensor is exposed to is detected by detection of the resonance frequency ($f_0$). The resonant frequency of the sensing circuit may also change in response to different environmental parameters including pressure.

In equation (2), the quality factor (Q) of the RLC circuit can be seen to be a function of R, L and C. Since the L is fixed and C is decided by equation (1), the R value can be determined by detection of Q. The R value allows determination of temperature based on principles analogous to those used for RTD. For example, in one embodiment for a parallel RLC sensing circuit the resistance of R can be 10 kohm at room temperature (e.g. 20° C.) for a particular material. But when the temperature changes, such as to 50° C., assume that the value of R changes to 11 kohm. A R-T relation which is generally linear (and can be vendor provided) allows temperature calibration for the particular resistor material, thus the temperature determined by measurement of the Q value. Furthermore, the $f_0$ and Q value can be detected remotely by wireless interrogation equipment. In equation (3), $f_0$ is the resonance frequency and $\Delta f$ is the frequency width of the half maximum points.

In the case of a parallel RLC circuit, equations for resonant frequency (fo) and Q value are as follows:

$$f_0 = \frac{1}{2\pi\sqrt{LC}} \quad (1)$$

$$Q = R\sqrt{\frac{C}{L}} \quad (4)$$

$$Q = \frac{f_0}{\Delta f} \quad (3)$$

The above equations show that only the Q calculation for the parallel RLC circuitry, equation 4, is different from that of the series RLC circuit. As with the series RLC circuit described above, when the humidity changes, the capacitance of the moisture sensitive capacitor changes which causes the resonance frequency $f_0$ for the parallel RLC circuit to change as well. As with the series RLC circuit, the resonance frequency is independent of the R value, and is only a function of the L and C values. As again with the series RLC circuit, since the L is fixed and C is decided by equation (1), the R value can be determined by detection of Q. As with the series embodiment, the R value allows determination of temperature based on principles analogous to those used for RTD.

FIG. 1A is a cross sectional view of a humidity sensor having temperature sensing 100 according to an embodiment of the invention formed on a substrate 101. Substrate can comprise a printed circuit board (PCB) having or more dielectric or ceramic layers, or a semiconducting substrate (e.g. silicon). Humidity sensor 100 comprises an RLC damped resonant circuit, comprising a capacitor 105 disposed on the topside of the substrate 101 having a first and a second plate 106, 107 interdigitated with one another (interdigitation better seen in FIG. 1B). The capacitor 105 can be embodied in a variety of layouts other than interdigitated electrodes. Another embodiment comprises side by side electrodes. The capacitor can be printed on substrate 101.

The plates 106 and 107 are separated by a moisture sensitive dielectric layer 110. The moisture sensitive dielectric can comprise a polymer, such as a polyimide. In another embodiment the moisture sensitive dielectric layer 110 comprises an inorganic material. The relative permittivity of water is about 81, and a moisture sensitive dielectric such as a polyimide between about 3 and 4. Accordingly, since the concentration of moisture in the dielectric increase with increasing humidity, the effective permittivity of the moisture sensitive coating increases in response to increased atmospheric moisture (humidity), generally increasing the capacitance of the capacitor which decreases the resonant frequency of the humidity sensor.

An RL network is on the bottomside of the substrate 101. The inductor 115 is configured in a closed loop (e.g. spiral) and is coupled by via 116 to plate 107 of capacitor 105. A temperature sensitive resistor portion 119 of the RL network is exclusive of any closed current paths and is coupled to the inductor 115 and plate 106 of the capacitor by via 117. An optional moisture permeable protection layer 120 is shown on top of the capacitor 105. In one embodiment, the moisture permeable protective layer comprises a nanoscale metal layer, such as a 10 to 200 nm metal layer for protection of the moisture sensitive dielectric layer 110 from deteriorating when it is directly exposed to the environment. In one particular embodiment the nanoscale metal layer comprises from 10 to 100 nm of platinum. In another embodiment, the moisture permeable protection layer comprises a porous ceramic layer.

Figure 1B:
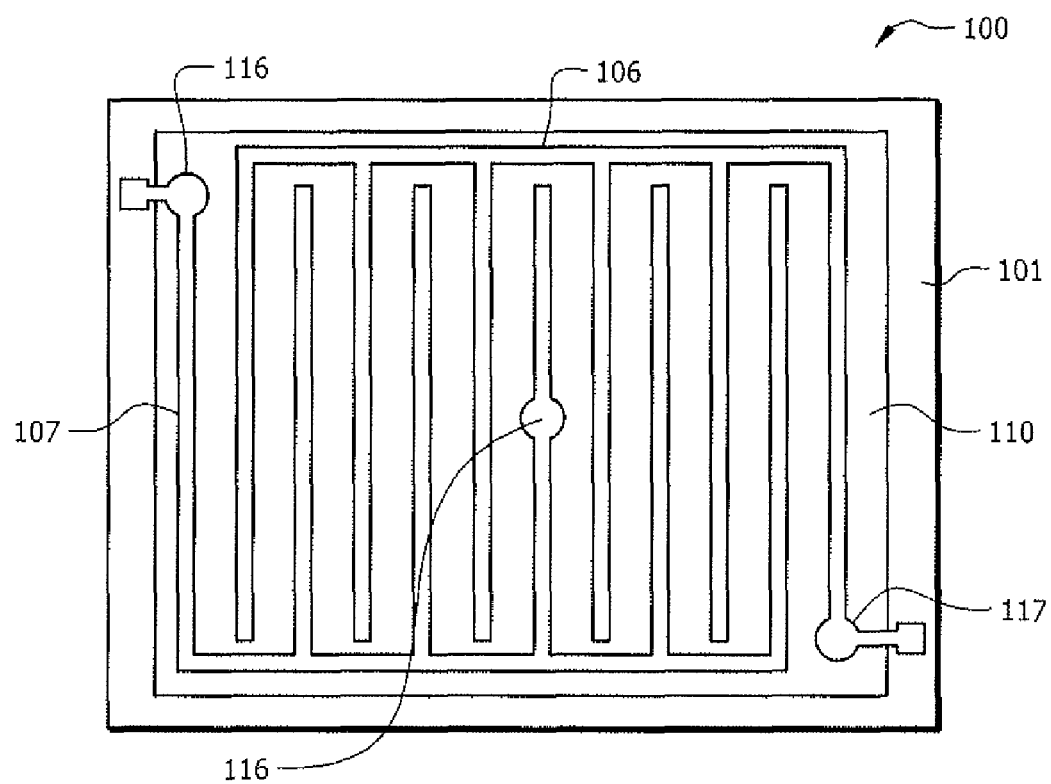
FIG. 1B is a top view of capacitor revealing interdigitated electrodes that can be used with humidity sensors according to an embodiment of the invention.

FIG. 1B is a top view of capacitor 100 revealing interdigitated electrodes 106 and 107. The optional protection layer 120 is not shown. An interdigitated arrangement is only one of many possible capacitor arrangements.

Figure 1C:
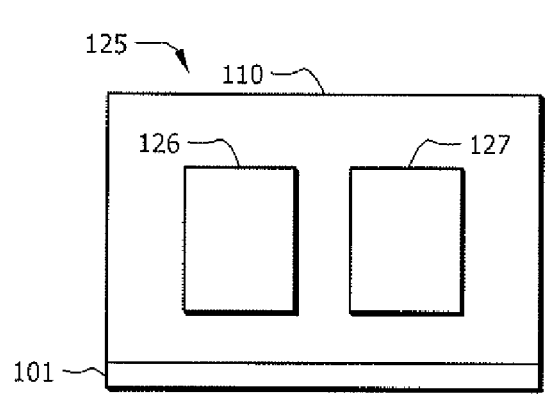
FIG. 1C is a top view of a capacitor having side-by-side electrodes that can be used with humidity sensors according to an embodiment of the invention.

FIG. 1C is a top view of a capacitor 125 having side-by-side electrodes 126 and 127 separated by dielectric layer 110. In one embodiment regions of dielectric layer 110 are removed and backfilled with a metal material to form plates 126 and 127, analogous to a damascene process.

Figure 1D:
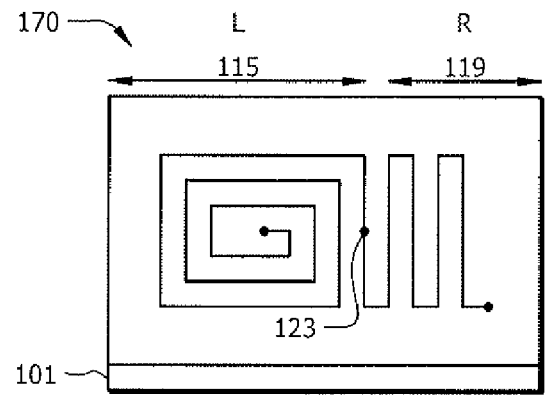
FIG. 1D is a top view of an exemplary RL network that can be used with humidity sensors according to an embodiment of the invention.

FIG. 1D is a top view of an exemplary RL network 170 comprising inductor 115 and resistor 119. In one particular embodiment inductor 115 comprises copper and resistor 119 comprises platinum. Inductor 115 and resistor 119 are connected together at contact 123.

It is generally advantageous to have the inherent parasitic series resistance of the inductor to be as small as possible because this resistive contribution will lower the Q of the RLC sensor, whether in a series or parallel RLC arrangement. A low parasitic capacitor is generally also helpful because parasitic capacitance reduces the sensitivity of the sensing capacitor on humidity. In order to decrease the parasitic resistance and capacitance of the inductor, the width of spiral or other closed inductor trace can be widened to reduce the parasitic resistance. However, a wider trace will increase the parasitic capacitance. As described below, multilayer humidity sensors according to embodiments of the invention provide an inductor that provides both a low parasitic resistance and a low parasitic capacitance.

Figure 2A:
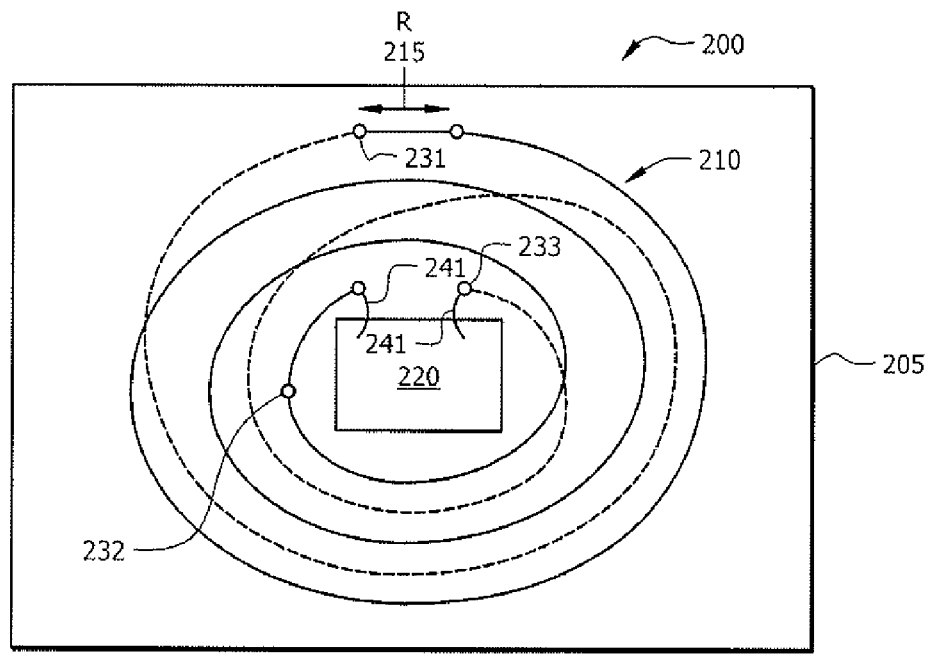
Figure 2B:
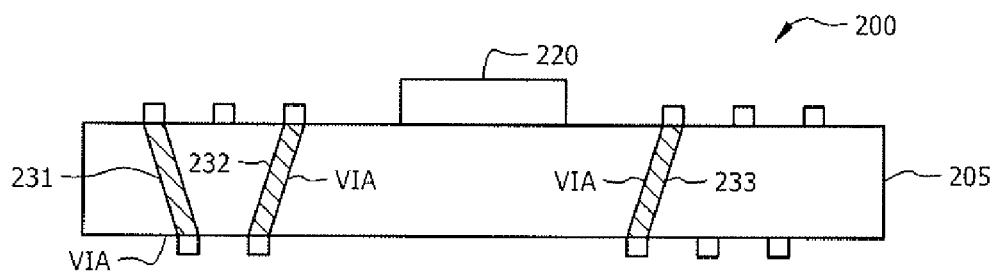
FIG. 2B shows a cross sectional view of the same sensor.

FIG. 2A shows a multi-substrate layer high Q series RLC humidity sensor 200, according to an embodiment of the invention comprising substrate 205, such as a printed circuit board (PCB) substrate, while FIG. 2B shows a cross sectional view of sensor 200. Sensor 200 can provide a high Q, such as from 30 to 100, or more.

Although only a single substrate 205 is shown, sensor 200 can comprise a plurality of substrate layers, such as embodied as a multi-layer PCB as described below relative to FIG. 2C.

Sensor 200 comprises spiral shaped inductor 210 having both a portion on the topside of substrate 205 and a portion on the bottom side of substrate 205. In order to reduce the emission in the sharp end of spiral pattern of inductor 210, a circular or elliptical layout pattern for the spiral is shown rather than a rectangle spiral. The bottomside portions of inductor 210 are shown with a dashed line. Attached to the end of the inductor spiral on the topside of substrate 205 is a resistor 215 section comprised of a different material, specifically a relatively highly temperature sensitive metal, such as platinum. Through several vias 231-233, the inductor portions on the topside and bottomside are connected together to form a single equivalent inductor. The via number and positions can be altered to reduce the parasitic resistance and increase the inductance of inductor 210. A capacitor 220 having a moisture sensitive dielectric (not shown) is on the topside of substrate 205 in the center of the inductor 210. Wire bonds 241, such as gold bond wires, are shown for coupling the inductor 210 to plates of the capacitor 220.

Figure 2C:
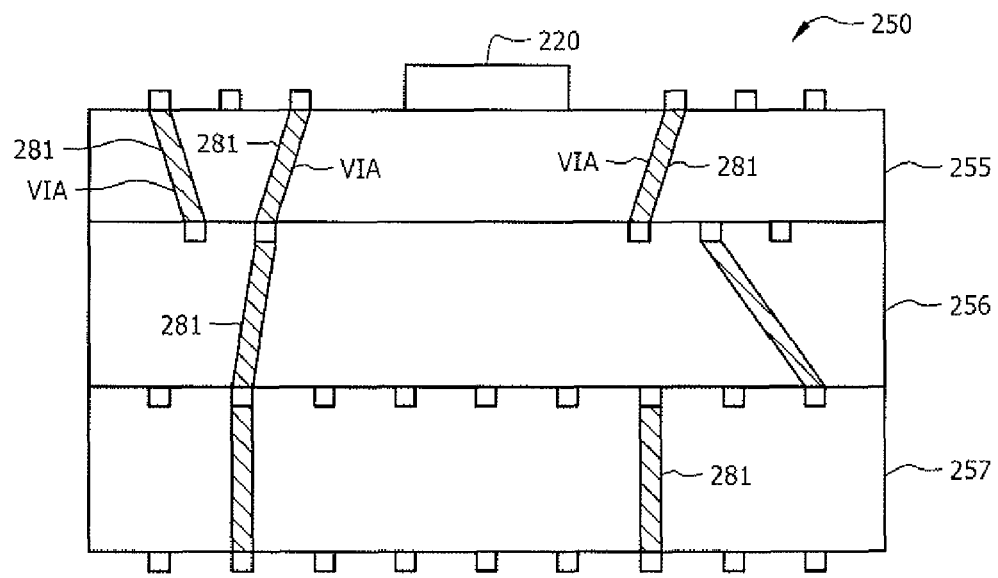
FIG. 2C shows a cross sectional view of multi-substrate layer sensor comprising a plurality of substrates stacked on one another.

FIG. 2C shows an example of cross sectional view of multi-substrate layer sensor 250 comprising substrates 255, 256, and 257 stacked on one another. Vias 281 extend to provide electrical connection between the respective layers 255-257 to form an inductor analogous to inductor 210 described in FIG. 2A. Sensor 250 will have a higher inductance and a smaller parasitic resistance as compared to single substrate layer-based sensors according to embodiments of the invention. Accordingly, multi-substrate layer sensors according to embodiments of the invention including sensor 250 will generally have a higher Q and thus provide higher sensor sensitivity to temperature changes as compared to single substrate layer sensors according to embodiments of the invention.

Interrogation equipment can be applied to couple a range of frequencies about the nominal oscillating frequency into the sensor through antenna coupling. By detection of frequency change of respective signals from LC tank, the humidity value can be detected and calculated. The resonant frequency ($f_o$) and the Q for RLC-based humidity sensors according to embodiments of the invention can be detected locally or remotely. The interrogation equipment generally scans a frequency range and receives the bounced back signals from the humidity sensor to detect the frequency shift. In the case of remote detection, the detection can be via a remotely located interrogation circuit comprising a single antenna or a pair of antennas (separate transmit and receive antenna). In the case of a single antenna, the interrogation equipment can transmit an interrogation signal at or near the resonance frequency towards the sensor device, then the equipment can be automatically switched to a receiving mode to detect signals including the frequency shift and for determining the Q value.

Within the interrogation zone, which is generally on the order of up to several meters depending on the resonance frequency and transmission power of interrogation equipment. In one embodiment of the invention the humidity sensor perturbs the impedance spectra of the interrogation circuit, from which the resonant frequency and the Q of the sensor can be determined, and this information used to provide a temperature compensated humidity value as described above.

Figure 3A:
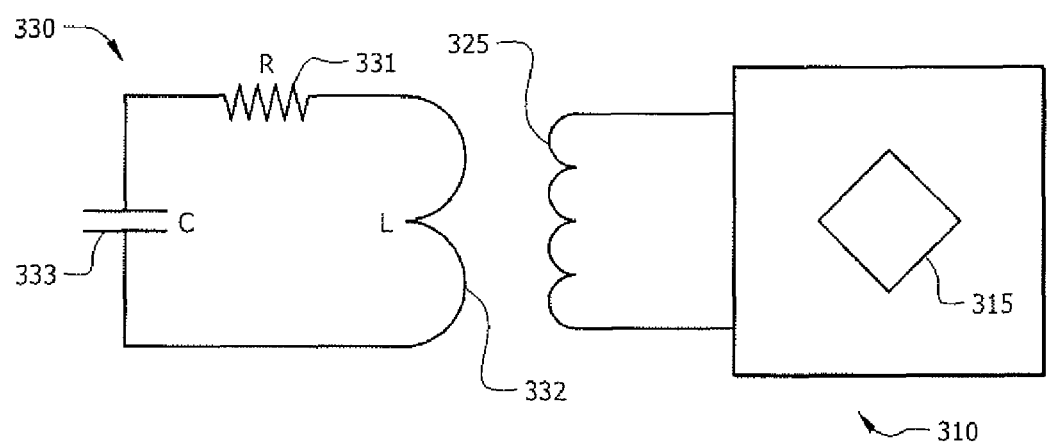
FIG. 3A shows a simplified depiction of interrogation system remotely monitoring a series RLC humidity sensor according to an embodiment of the invention.

FIG. 3A shows a simplified depiction of interrogation system 310 remotely monitoring a series RLC humidity sensor 320 according to an embodiment of the invention. Interrogation system 310 comprises function generator 315 and various electronics (e.g. amplifiers, filters, etc., not shown) coupled to coupling antenna 325. Interrogation equipment 310 interrogates an RLC series humidity sensor according to an embodiment of the invention 330 comprising resistor 331, inductor 332 and capacitor 333 to determine the resonant frequency and Q of the sensor 330. The inductor 332 can act as an antenna. The interrogation frequency range is generally centered around the resonant frequency of the RLC circuit, such as on the order of several MHz and generally up to the GHz range. As described above, detection of the resonant frequency $f_o$ provides the humidity and Q of the sensor 330 allows calculation of temperature through the resistance of resistor, which based on resistance-temperature calibration data, allows the temperature to be determined. The temperature allows the relative humidity to be corrected for the temperature around the sensor. The temperature can be reported itself as a parameter as well.

Figure 3B:
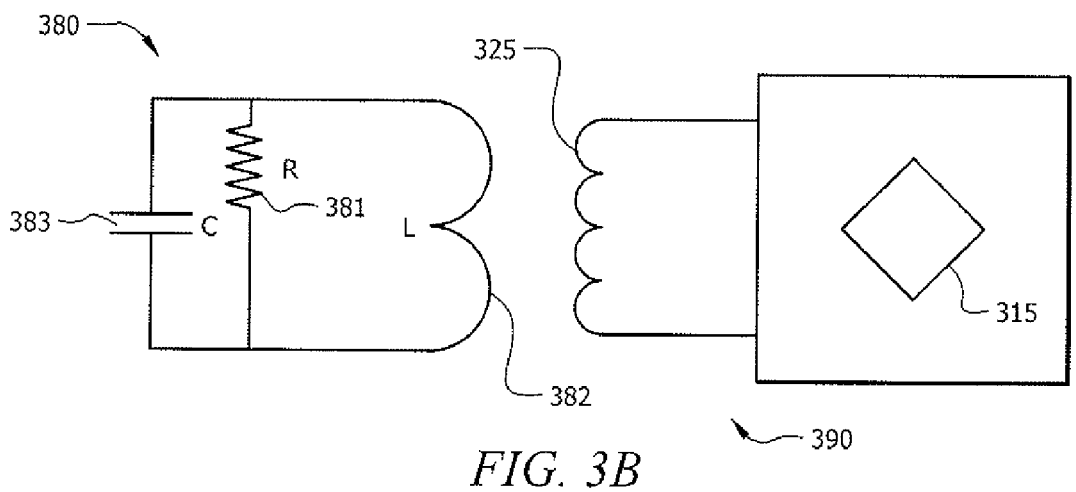
FIG. 3B shows a simplified depiction of interrogation system remotely monitoring a parallel RLC humidity sensor according to an embodiment of the invention.

FIG. 3B shows a simplified depiction of interrogation system 390 remotely monitoring a parallel RLC humidity sensor according to an embodiment of the invention. Interrogation equipment 390 interrogates an RLC series humidity sensor 380 according to an embodiment of the invention comprising resistor 381, inductor 382 and capacitor 383 to determine the resonant frequency and Q of the sensor 380.

Figure 4A:
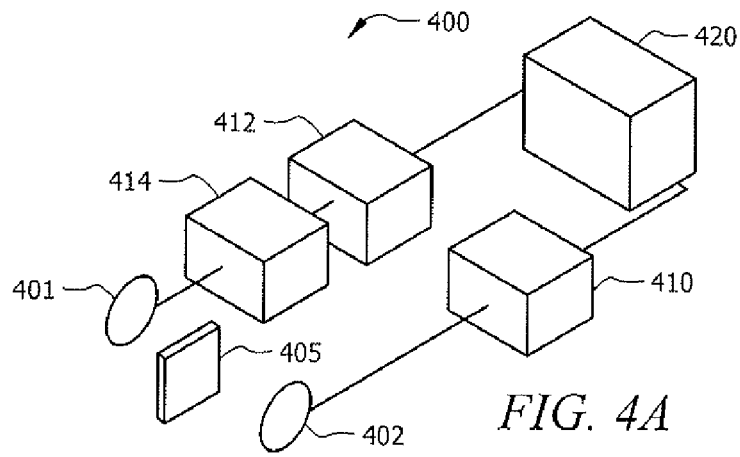
FIG. 4A shows a monitoring arrangement according to an embodiment of the invention having a pair of antennas, one for transmitting signals to the sensor and one for receiving signals from sensor, according to an embodiment of the invention.

FIG. 4A shows a monitoring arrangement 400 according to an embodiment of the invention having a pair of antennas 401 and 402, one for transmitting signals to sensor 405 and one for receiving signals affected by from sensor 405. The antennas can be a variety of antennas, including slots and loops. Monitoring arrangement 400 monitors the sensor over a defined region between two antennas 401 and 402. A function generator 410 is used to generate electromagnetic waves from antenna 402. The output voltage of the other receiving antenna 401 can be recorded using a lock-in amplifier 412 which can be coupled to a pre-amplifier 414. A computer or processor 420 is used to sweep the frequency of the interrogation field, collect data from the lock-in amplifier 412, and provide an analyzer function to determine the resonant frequency and Q of the sensor 405 placed within the interrogation zone. The distance over which the sensor 405 can be monitored depends upon the frequency which is centered at the resonant frequency of the sensor 405, the size of the sensor 405 relative to the antenna size, power levels, and background electromagnetic interference (EMI). This sensor monitoring approach is suitable for applications where the antennas can be placed about or around the testing area.

Figure 4B:
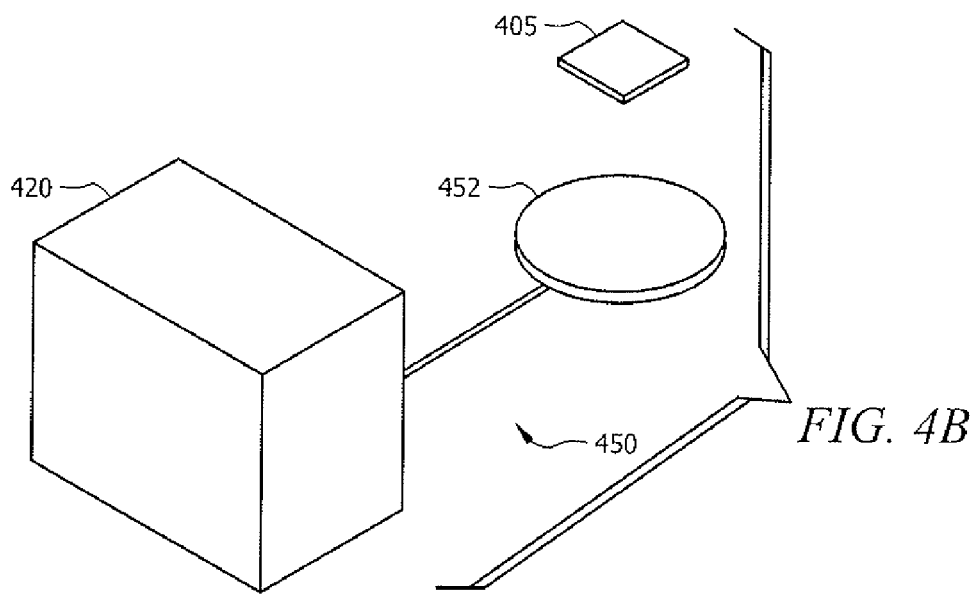
FIG. 4B shows a monitoring arrangement according to another embodiment of the invention that utilizes a single antenna one for both transmitting signals to the sensor and receiving signals from the sensor, according to an embodiment of the invention.

FIG. 4B shows a monitoring arrangement 450 according to another embodiment of the invention that utilizes a single antenna 452, such as a multi-turn loop antenna. The angular spread over which the sensor 455 can be monitored is generally increased as compared to arrangement 400.

Sensors according to embodiments of the invention generally have only inexpensive components and do not require a power source such as a battery. Such sensors be designed and built at low cost and can be disposable. Although the interrogation equipment can be relatively expensive, the interrogation equipment can function to interrogate a plurality of humidity sensors. Moreover, since there is no wire or battery generally required for sensors according to embodiments of the invention, the sensor can be used in applications having limited space, such as for most medical applications, including for patient breathing detection.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

1. Series RLC Circuitry

Parameter Selection:

Parameter selection for series RLC circuitry can be in a wide range. Below is one example for parameters and the resulting resonant frequency $f_0$.

| L (nH) | C (pF) | $f_0$ (Hz) |
| --- | --- | --- |
| 100 | 100 | 50329212.16 |
| 100 | 90 | 53051647.76 |
| 100 | 80 | 56269769.82 |

When the humidity changes, the capacitance changes which changes the resonance frequency $f_0$ as shown above.

| Temperature | L (nH) | R (Ohm) | C (pF) | Q |
| --- | --- | --- | --- | --- |
| 25 deg C. | 100 | 1 | 100 | 31.62278 |
| 35 deg C. | 100 | 1.1 | 100 | 28.74798 |

When the value of the resistor is 1 ohm at 25° C. and the temperature changes from 25 to 35° C., the resistance increases by 10% to 1.1 ohms, and as a result the Q value will change as shown above.

2. Parallel RLC Circuitry

Parameter Selection:

Parameter selection of parallel RLC circuitry can generally be in a wide range.

Below is one example for parameters and the resulting resonant frequency $f_0$.

| L (nH) | C (pF) | $f_0$ (Hz) |
| --- | --- | --- |
| 100 | 100 | 50329212.16 |
| 100 | 90 | 53051647.76 |
| 100 | 80 | 56269769.82 |

When the humidity changes, the capacitance changes, which changes the resonance frequency $f_0$ as shown above.

| temperature | L (nH) | R (kOhm) | C (pF) | Q |
| --- | --- | --- | --- | --- |
| 25 deg C. | 100 | 10 | 100 | 316.2278 |
| 35 deg C. | 100 | 11 | 100 | 347.8505 |

When the value of the resistor is 10 kohm at 25° C. and the temperature increases by 10° C., the resistance changes to 11 kohm, and as a result the Q value will change as shown above.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In particular regard to the various functions performed by the above described components (assemblies, devices, circuits, systems, etc.), the terms (including a reference to a "means") used to describe such components are intended to correspond, unless otherwise indicated, to any component which performs the specified function of the described component (e.g., that is functionally equivalent), even though not structurally equivalent to the disclosed structure which performs the function in the herein illustrated exemplary implementations of the invention. In addition, while a particular feature of the invention may have been disclosed with respect to only one of several implementations, such feature may be combined with one or more other features of the other implementations as may be desired and advantageous for any given or particular application. Furthermore, to the extent that the terms "including", "includes", "having", "has", "with", or variants thereof are used in either the detailed description and/or the claims, such terms are intended to be inclusive in a manner similar to the term "comprising."

The invention claimed is:

1. A humidity sensor having temperature sensing, comprising:
   a substrate;
   a resonant RLC circuit formed in or on said substrate, said resonant circuit comprising:
   a capacitor having a first and a second electrically conductive plate and a moisture sensitive dielectric interposed between said first and said second plate;
   an RL network comprising an inductor and a resistor coupled to said capacitor comprising a high relative temperature coefficient of resistance (TCR) portion formed from a first material coupled to a low relative TCR portion formed from a second material different from said first material.

2. The humidity sensor of claim 1, wherein said RLC circuit comprises a series RLC circuit.

3. The humidity sensor of claim 1, wherein said RLC circuit comprises a parallel RLC circuit.

4. The humidity sensor of claim 1, wherein said high relative temperature coefficient of resistance (TCR) portion is separate from said inductor being in a non-inductive geometry being exclusive of any closed current paths.

5. The humidity sensor of claim 1, wherein said high relative temperature coefficient of resistance (TCR) portion is integrated with said inductor being in an inductive geometry comprising at least one closed current path.

6. The humidity sensor of claim 1, wherein said substrate comprises a plurality of substrates stacked on one another and said inductor comprises a multi-layer inductor comprising at least a first and a second layer electrically connected to one another by a plurality of vias through said plurality of substrates.

7. The humidity sensor of claim 1, wherein said first material comprises primarily by weight platinum or nickel.

8. The humidity sensor of claim 1, wherein said substrate comprises a printed circuit board (PCB).

9. The humidity sensor of claim 1, wherein said first and said second plates of said capacitor are located side-by-side.

10. The humidity sensor of claim 1, wherein said first and said second plates of said capacitor are interdigitated with one another.

11. The humidity sensor of claim 1, wherein said moisture sensitive dielectric comprises a polymer comprising material.

12. The humidity sensor of claim 11, said polymer comprises a polyimide.

13. The humidity sensor of claim 1, further comprising a moisture permeable protective layer over said capacitor.

14. The humidity sensor of claim 13, wherein said moisture permeable protective layer comprises a nanoscale metal layer.

15. The humidity sensor of claim 14, wherein said nanoscale metal layer comprises 10 to 100 nm of platinum.

16. A method of temperature compensated humidity sensing, comprising:
   exposing a resonant RLC circuit comprising an inductor, a capacitor, and a resistor to environmental conditions including a temperature and a relative humidity, wherein said capacitor comprises a first and second plate and a moisture sensitive dielectric interposed between said plates;
   measuring a resonant frequency value of said resonant circuit following said exposing;
   determining a relative humidity value from said resonant frequency value;
   measuring a quality factor (Q) value of said resonant circuit following said exposing;
   determining said temperature from said Q value, and
   adjusting said relative humidity value based on said temperature.

17. The method of claim 16, wherein said determining said relative humidity value comprises calculating a change in said resonant frequency from said resonant frequency value and a predetermined reference resonant frequency value.

18. The method of claim 16, wherein said determining said temperature comprises calculating a change in said Q from said Q value and a predetermined reference Q value and determining a change in a resistance of said resonant circuit from said change in said Q.

19. The method of claim 16, wherein said measuring said resonant frequency and said measuring said temperature comprises transmitting electromagnetic interrogation signals from remotely located interrogation equipment comprising a generator coupled to at least one antenna.

20. The method of claim 19, wherein said electromagnetic interrogation signals span a range of frequencies and said interrogation equipment includes an impedance analyzer.

* * * * *